United States Patent [19]

Adams et al.

[11] Patent Number: 5,792,891
[45] Date of Patent: Aug. 11, 1998

[54] INTEGRATED PROCESS FOR THE PRODUCTION OF TAME

[75] Inventors: John R. Adams; Lawrence A. Smith, Jr.; Dennis Hearn, all of Houston; Edward M. Jones, Jr., Friendswood; Robert P. Arganbright, Seabrook, all of Tex.

[73] Assignee: Catalytic Distillation Technologies, Pasadena, Tex.

[21] Appl. No.: 792,980

[22] Filed: Feb. 3, 1997

Related U.S. Application Data

[60] Provisional application No. 60/011,421 Feb. 9, 1996.

[51] Int. Cl.⁶ ............................................... C07C 41/06
[52] U.S. Cl. ........................ 568/697; 585/614; 585/616; 585/601; 585/649; 585/654; 422/191
[58] Field of Search ............................ 568/697; 585/614, 585/616, 601, 649, 654

[56] References Cited

U.S. PATENT DOCUMENTS

| | | | |
|---|---|---|---|
| 3,558,733 | 1/1971 | Myers | 260/683.2 |
| 3,631,219 | 12/1971 | Myers | 260/683.2 |
| 4,361,422 | 11/1982 | Derrien et al. | 44/56 |
| 4,436,949 | 3/1984 | Myers et al. | 585/664 |
| 4,754,078 | 6/1988 | Vora et al. | 568/697 |
| 5,043,523 | 8/1991 | Hsing | 585/664 |
| 5,431,888 | 7/1995 | Hickey et al. | 422/191 |
| 5,595,634 | 1/1997 | Hearn et al. | 203/29 |

OTHER PUBLICATIONS

Perrin et al; Purification of Laboratory Chemicals;second edition; p. 26, lines 39–41, 1980.
Alumina: Catalyst & Support. Pines, et al. vol. 82, pp. 2471–2483. May 1960.
High Purity AluminaI. Tung et al. vol. 3, pp. 229–238. 1964.

*Primary Examiner*—Gary Geist
*Assistant Examiner*—Sreeni Padmanabhan
*Attorney, Agent, or Firm*—Kenneth H. Johnson

[57] ABSTRACT

An alkene skeletal isomerization process is employed in an integrated process for the production of tertiary ether, e.g., tertiary amyl methyl ether (TAME) from the reaction of isoamylenes ($iC_5^=$'s) with methanol in the presence of an acid cation exchange resin. A light naphtha from a fluid catalytic cracking unit is used as the source of the $iC_5^=$'s in a process which separates the $C_5$ containing fraction from the light naphtha, selectively hydrogenates the di-olefins contained in the $C_5$ containing fraction, reacts the $iC_5^=$'s contained in the $C_5$ containing fraction with methanol to form TAME, separates the TAME from the unreacted materials as a product, separates methanol from the unreacted materials, isomerizes a portion of the $nC_5^=$'s to $iC_5^=$'s , for example using a zeolite or an alumina treated with methanol, and use of the isomerization product as feed for a TAME reactor.

15 Claims, 2 Drawing Sheets

INTEGRATED PROCESS FOR THE PRODUCTION OF TAME

This application claims the benefit of U.S. Provisional Application Ser. No. 60/011,421 filed Feb. 9, 1996.

BACKGROUND OF THE INVENTION

1. Field of the Invention

The present invention relates to an integrated process to upgrade $C_5$ refinery cuts, more particularly the upgrading of $C_5$ olefins to useful octane improvers, specifically by the production of tertiary amyl methyl ether (TAME) from the reaction of isoamylenes ($iC_5^=$'s) with methanol in the presence of an acid cation exchange resin.

2. Related Information

The $C_5$ refinery cut is valuable as a gasoline blending stock or as source of isoamylene to form an ether by reaction with lower alcohols. The Clean Air Act and regulations implementing it require the reformulation of gasoline. Requirements for reformulated gasolines include the reduction of benzene and olefins. The reformulation has resulted in the loss of octane in the straight gasoline. Other requirements are (1) to include a certain amount of "oxygenates", such as methyl tertiary butyl ether (MTBE), TAME, tertiary amyl ethyl ether (TAEE) or ethanol, (2) to reduce the amount of olefins and aromatics in gasoline, and (3) to reduce the vapor pressure (volatility). Refiners have elected to meet these federal mandates by preferably using the ethers. The demand for MTBE has in some areas has out stripped the available isobutene. Some refiners are looking to the $C_5$ cuts which contain suitable isopentene for producing TAME and TAEE. In addition to improving air quality by adding the ether rather than the raw ethanol, which has a somewhat higher volatility, and removing the olefins, the replacement of the pentenes with the ethers results in an increase in the octane rating of the stream.

The $C_5$'s in the feed to a TAME/TAEE unit are contained in a single "light naphtha" cut which contains everything from $C_5$'s through $C_8$'s and higher. This mixture can easily contain 150 to 200 components and thus identification and separation of the products is difficult. For this reason the TAME/TAEE is not generally separated from the heavier components, but all are used directly as octane blending stocks.

Several of the minor components (diolefins) in the feed will react slowly with oxygen during storage to produce "gum" and other undesirable materials. However, these components also react very rapidly in the TAME/TAEE process to form a yellow, foul smelling gummy material. Thus, it is seen to be desirable to remove these components whether the "light naphtha" cut is to be used only for gasoline blending by itself or as feed to the TAME/TAEE process.

Mixed refinery streams often contain a broad spectrum of olefinic compounds. This is especially true of products from either catalytic cracking or thermal cracking processes. Refinery streams are usually separated by fractional distillation, and because they often contain compounds that are very close in boiling points, such separations are not precise. A $C_5$ stream, for instance, may contain $C_4$'s and up to $C_8$'s. These components may be saturated (alkanes), unsaturated (mono-olefins), or poly-unsaturated (diolefins). Additionally, the components may be any or all of the various isomers of the individual compounds.

In most $C_5$ cuts the isoamylene suitable for the production of TAME or TAEE is frequently present in small quantities, e.g. less than 15%, whereas there are other $C_5$ olefins isomers and enough dienes and acetylenes to inhibit the etherification process. In the present process the valuable ether production is maximized while removing olefins and other impurities found in the $C_5$ cuts. It is an advantage of the present process that the production of TAME/TAEE from $C_5$ cuts is maximized. It is a particular feature of the present invention that the treated components can be reblended with the raffinate of the $C_5$ cuts to provide an upgraded gasoline blending stream. It is a further advantage of the present invention that the raffinate stream is substantially upgraded by the reduction of olefinic content.

SUMMARY OF THE INVENTION

Briefly the present invention comprises the steps of hydrotreating/isomerization of a $C_5$ stream containing alkanes, normal olefins, diolefins and reactive and inactive isoolefins to reduce diolefins and isomerize inactive isoolefin isomers into reactive isoolefins, recovering the stream having a reduced diolefin content and an enhanced reactive isoolefin content, etherifying the reactive isoolefins in the stream, separating the ether from the normal olefins, and isomerizing a portion of the normal olefins to isoolefins, etherifying a portion said isoolefins and recovering ether and a raffinate comprising principally alkanes.

DETAILED DESCRIPTION OF THE INVENTION

Glossary

For clarification purposes definitions of the following terms and abbreviations are provided:

FCC—fluid catalytically cracked or from a refinery fluid catalytic cracker.

$iC_5$'s—the various isomers of saturated five carbon hydrocarbons.

$nC_5$—normal pentane.

$iC_5^=$'s—the various isomers of unsaturated five carbon hydrocarbons having one double bond.

$nC_5^=$—normal pentene.

TAME—tertiary amyl methyl ether which is the reaction product of the various $iC_5^=$ isomers with methanol.

TAEE—tertiary amyl ethyl ether which is the reaction product of the various $iC_5^=$ isomers with methanol.

PROCESS

The integrated process of the present invention combines selective hydrogenation of dienes, etherification, and the skeletal isomerization of normal olefins. This is shown in the attached figure to which the reader is referred for a description of the integrated process.

In one embodiment the invention relates to the use of a light naphtha from a fluid catalytic cracking unit as the source of the $iC_5^=$'s in a process which separates the $C_5$ containing fraction from the light naphtha, selectively hydrogenates the di-olefins contained in the $C_5$ containing fraction, reacts the $iC_5^=$'s contained in the $C_5$ containing fraction with methanol to form TAME, separates the TAME from the unreacted materials as a product, isomerizes a portion of the $nC_5^=$'s to $iC_5^=$'s and send the combined $C_5$ stream to a second etherification; or alternatively separates the normal pentenes ($nC_5^=$'s) from the unreacted material, isomerizes a portion of the $nC_5^=$'s to $iC_5^=$'s and recycles the isomerization product to the TAME reactor.

In addition to monoolefins olefins having more than one double bond and the acetylenic compounds (having a triple bond) are present and have lesser uses and are detrimental to many of the chemical process in which the single double bond compounds are used, for example etherification.

In one embodiment of the process is a new method for the isomerization of normal olefins such as the pentenes and butenes is carried out using an alumina catalyst treated with methanol. This aspect of the present invention relates to a process of improving catalyst selectivity and yield for the isomerization of alkenes in the presence of an alumina catalyst by contacting said an alumina catalyst with methanol. The alumina catalyst may be contacted with the methanol intermittently or continuously with the alkene. The methanol may also be applied to the catalyst in the absence of the alkenes.

The isomerization is carried out by feeding the alkene containing stream in vapor phase to a reactor containing the alumina catalyst either with the methanol, continuously or intermittently or after the catalyst has been treated with the methanol. When methanol is added continuously to said feed stream containing alkenes an amount of from about 0.001 to 0.1 weight percent of the feed stream may be used. When the methanol is added intermittently, either with the alkene feed or alone, and amount equal to 0.05 to 0.25 weight % of the catalyst may be added, generally at intervals of 40 to 100 hours.

In one embodiment the invention may be described as an integrated process for the maximum production of tertiary amyl methyl ether (TAME) utilizing a light naphtha stream from a fluid catalytic cracking unit. The process comprises the steps of:

(a) feeding a first stream comprising a naphtha from a fluid catalytic cracking unit and a second stream comprising hydrogen to a first distillation column reactor containing a hydrogenation catalyst in a first catalytic distillation structure in the upper portion thereof and inert distillation structure in the lower portion thereof;

(b) concurrently in said first distillation column reactor
  (i) separating the fraction of said naphtha containing the $C_5$'s and lower boiling materials from the $C_6$ and higher boiling materials in said lower portion by fractional distillation, said $C_5$ containing fraction comprising $iC_5$'s, $nC_5$'s, $iC_5^=$'s, $nC_5^=$'s, and $C_5$ diolefinic materials,
  (ii) contacting said $C_5$ containing fraction with said catalytic distillation structure to react said $C_5$ diolefinic materials contained within said $C_5$ containing fraction with hydrogen to convert said diolefinic materials to mono-olefins,
  (iii) removing said $C_6$ and higher boiling materials from said first distillation column reactor as a first bottoms, and
  (iv) removing said $C_5$ containing fraction from said distillation column reactor as a first overheads;

(c) preferably feeding said first overheads and a stream containing methanol to a first straight pass fixed bed reactor etherification reactor containing an acid cation exchange resin to react a portion of the $iC_5^=$'s with said methanol to produce an effluent containing tertiary amyl methyl ether, methanol and unreacted $iC_5^=$'s and other unreacted materials;

(d) feeding said effluent to a second distillation column reactor containing a second catalytic distillation structure comprising an acid cation exchange resin;

(e) concurrently in said second distillation column reactor:
  (i) contacting said effluent with said second catalytic distillation structure thereby reacting a portion of said $iC_5^=$'s with methanol to form additional tertiary amyl methyl ether,
  (ii) separating methanol and the remaining unreacted materials from the tertiary amyl methyl ether produced in said first fixed bed reactor and in said second distillation column reactor by fractional distillation,
  (iii) recovering said tertiary amyl methyl ether as a second bottoms from said second distillation column reactor, and
  (iv) recovering said methanol and remaining unreacted materials comprising $nC_5^=$ as a second overheads;

(f) feeding said second overheads to a straight pass fixed bed reactor containing an alumina isomerization catalyst treated with methanol to produce an effluent containing $iC_5^=$'s;

(g) preferably feeding said effluent from (f) and a stream containing methanol to a second straight pass fixed bed reactor etherification reactor containing an acid cation exchange resin to react a portion of the $iC_5^=$'s with said methanol to produce an effluent containing tertiary amyl methyl ether, methanol and unreacted $iC_5^=$'s and other unreacted materials;

(h) feeding said effluent from said second straight pass etherification reactor to a third distillation column reactor containing a third catalytic distillation structure comprising an acid cation exchange resin; and (i) concurrently in said third distillation column reactor:
  (i) contacting said effluent from (g) with said third catalytic distillation structure thereby reacting a portion of said $iC_5^=$'s with methanol to form additional tertiary amyl methyl ether,
  (ii) separating methanol and the remaining unreacted materials from the tertiary amyl methyl ether produced in said second fixed bed reactor and in said third distillation column reactor by fractional distillation,
  (iii) recovering said tertiary amyl methyl ether as a second bottoms from said third distillation column reactor, and
  (iv) recovering said methanol and remaining unreacted materials as a second overheads.

In an alternative embodiment the isomerization product may be fed to the first etherification units (fixed bed and catalytic distillation reactor) thus eliminating the second etherification unit. This embodiment may be used if slip stream or some other means is provided to prevent a build up of unreacted materials in the recycle to the etherification step.

Preferably the naphtha stream is treated to remove the light organic sulfur compounds such as hydrogen sulfide and mercaptans. One common treatment for removal of these compounds is the MEROX process, which is basically a caustic wash and which is well known in the industry.

Although highly desirable, the fixed bed etherification units are not required to carry out the process and only the distillation reactors may be used. The fixed bed etherification reactor is preferably operated as a "boiling point reactor" as described in U.S. Pat. No. 4,950,803 which is incorporated herein by reference. That is, the pressure of the fixed bed reactor is adjusted such that the reaction mixture is boiling. This conveniently removes the heat produced by the exothermic reaction of $iC_5^=$'s with the methanol as latent heat of vaporization aiding in preventing an increase in the temperature.

The unreacted methanol is removed, if desired, from the other unreacted material in the overheads from the second and third distillation column reactor by water washing and subsequent distillation of the methanol water mixture. The recovered methanol may be recycled to the fixed bed reactor and the water to the water wash. However, since the skeletal isomerization of the $nC_5^=$'s ma be carried out in the presence of methanol, only the methanol not desired in the isomerization needs to be removed. In some catalytic distillations operated at below stoichiometric amounts of methanol, it may be necessary to add methanol to the isomerization. It is one advantage of the present invention, both the integrated process and the isomerization that the water wash to remove methanol may be eliminated or reduced in size and cost.

HYDROGENATION

Hydrogenation is the reaction of hydrogen with a carbon-carbon multiple bond to "saturate" the compound. This reaction has long been known and is usually done at superatmospheric pressures and moderate temperatures using an excess of hydrogen over a metal catalyst. Among the metals known to catalyze the hydrogenation reaction are platinum, rhenium, cobalt, molybdenum, nickel, tungsten and palladium. Generally, commercial forms of catalyst use supported oxides of these metals. The oxide is reduced to the active form either prior to use with a reducing agent or during use by the hydrogen in the feed. These metals also catalyze other reactions, most notably dehydrogenation at elevated temperatures. Additionally they can promote the reaction of olefinic compounds with themselves or other olefins to produce dimers or oligomers as residence time is increased.

Selective hydrogenation of hydrocarbon compounds has been known for quite some time. Peterson, et al in "The Selective Hydrogenation of Pyrolysis Gasoline" presented to the Petroleum Division of the American Chemical Society in September of 1962, discusses the selective hydrogenation of $C_4$ and higher diolefins. Boitiaux, et al in "Newest Hydrogenation Catalyst", Hydrocarbon Processing, March 1985, presents a nonenabling overview of various uses of hydrogenation catalysts, including selective hydrogenation, utilizing a proprietary bimetallic hydrogenation catalyst.

An additional feature of the hydrogenation is that a portion of the mono-olefins contained within the stream or produced by the selective hydrogenation of the diolefins may be isomerized to more desirable products. This is particularly true with regard to the $iC_5^=$ where some of the isoolefin isomers are non reactive for the etherification. Isomerization can be achieved with the same family of catalysts as used in hydrogenations. Generally the relative rates of reaction for various compounds are in the order of from faster to slower:

(1) hydrogenation of diolefins (2) isomerization of the mono-olefins (3) hydrogenation of the mono-olefins.

It has been shown generally that in a stream containing diolefins, the diolefins will be hydrogenated before isomerization occurs. It has also been found that very low total pressures may be used for optimal results in some of the present hydrogenations, preferably in the range of 50 to 150 psig with the same excellent results and low hydrogen partial pressure, i.e., less than 50 psia, for example 0.1–10 psia. Both higher and lower pressures within the broad range may be used may be used with satisfactory results.

Broadly stated, the catalytic material is a component of a distillation system functioning as both a catalyst and distillation packing, i.e., a packing for a distillation column having both a distillation function and a catalytic function.

The reaction system can be described as heterogenous since the catalyst remains a distinct entity. Any suitable hydrogenation catalyst may be used, for example Group VIII metals of the Periodic Table of Elements as the principal catalytic component, alone or with promoters and modifiers such as palladium/gold, palladium/silver, cobalt/zirconium, nickel preferably deposited on a support such as alumina, fire brick, pumice, carbon, silica, resin or the like.

A preferred catalytic material comprises palladium oxide, preferably 0.1 to 5.0 weight %, supported on an appropriate support medium such as alumina, carbon or silica, e.g., ⅛" alumina extrudates. In a preferred catalytic distillation structure the particulate catalyst material is disposed within a porous plate or screen to contain the catalyst and provide a distillation surfaces, in the form of a wire mesh structure, such as a wire mesh tubular structure or any other similar structure.

A preferred catalyst structure for the present hydrogenation reaction comprising flexible, semi-rigid open mesh tubular material, such as stainless steel wire mesh, filed with a particulate catalytic material in one of several embodiments recently developed in conjunction with the present process.

One new catalyst structure developed for use in hydrogenations is described in U.S. Pat. No. 5,266,546 which is incorporated herein in its entirety. U.S. Pat. No. 4,242,530 and U.S. Pat. No. 4,443,559 which are incorporated herein, disclose supported catalyst in a plurality of pockets in a cloth belt or wire mesh tubular structures, which is supported in the distillation column reactor by open mesh knitted stainless steel wire by twisting the two together into a helix, which have been used.

A preferred catalytic distillation structure comprises a particulate catalyst containing 0.1 to 1.0 weight per cent palladium on an alumina support with the catalyst placed in the pockets of a suitable support such as a cloth belt. In a preferred embodiment the supported palladium oxide catalyst is contained in wire mesh containers and loaded into the distillation reaction zone. The present hydrogenation step preferably operates at overhead pressure of said distillation column reactor in the range between 0 and 250 psig and temperatures within said distillation reaction zone in the range of 100° to 300° F., preferably 130° to 270° F.

A catalyst suitable for the present hydrogenation is 0.34 wt % Pd on 3 to 8 mesh $Al_2O_3$ (alumina) spheres, supplied by United Catalysts Inc. designated as G-68C. Typical physical and chemical properties of the catalyst as provided by the manufacturer are as follows:

TABLE I

| Designation | G-68C |
| --- | --- |
| Form | Sphere |
| Nominal size | 5 × 8 mesh |
| Pd. wt % | 0.3 (0.27–0.33) |
| Support | High purity alumina |

The light naphtha is fed to the distillation column reactor below the catalyst packing. The hydrogen is fed as a gas at or near the bottom of the bed of catalyst packing. After the reaction has started the heat of reaction, which is exothermic, causes additional vaporization of the mixture in the bed. Vapors are taken overhead and substantially all of the condensible material is condensed to a temperature of 100° F. The condensed material is collected and separated from non condensibles, such as the unreacted hydrogen. A portion of the condensed materials are returned to the top of the distillation column reactor as reflux. The distillate product is a suitable feed for a TAME reactor. The uncondensible material is vented and for economy the hydrogen can recycled to the reactor.

Bottoms product containing essentially no $C_5$ diolefins is withdrawn may be sent to gasoline blending as stable gasoline.

ETHERIFICATION

U.S. Pat. Nos. 5,003,124 and 4,950,803 disclose a liquid phase process for the etherification of $C_4$ and $C_5$ isoolefins with $C_1$ to $C_6$ alcohols in a boiling point fixed bed reactor that is controlled at a pressure to maintain the reaction mixture at its boiling point which may be directly attached to a catalytic distillation reactor.

The catalytic distillation process employs a catalyst system (See U.S. Pat. Nos. 4,215,011 and 4,302,356) which provides for both reaction and distillation concurrently in the same reactor, at least in part within the catalyst system. The method involved is briefly described as one where concurrent reaction and distillation occur in a combination reactor-distillation structures are described in several U.S. Patents, namely U.S. Pat. Nos. 4,242,530; 4,250,052; 4,232,177; 4,302,356; 4,307,254; and 4,336,407. Additionally U.S. Pat. Nos. 4,302,356 and 4,443,559 disclose catalyst structures which are useful as distillation structures.

For example, in this system and procedure, methanol and isoamylene (or the stream from the boiling point reactor which contains, ether, some unreacted isoolefin and methanol or make up methanol) containing $C_5$ stream are continuously fed to the reactor/distillation column where they are contacted in the catalytic distillation structure. The methanol preferentially reacts with isoamylene, forming TAME which is heavier than the $C_5$ components of the feed and the methanol, hence it drops in the column to form the bottoms. Concurrently, the unreacted $C_5$'s (e.g. n-pentane, n-pentenes are lighter and form an overhead.

Catalysts preferred for the etherification process are cation exchangers, which contain sulfonic acid groups, and which have been obtained by polymerization or copolymerization of aromatic vinyl compounds followed by sulfonation.

The resulting products preferably contain an average of 1.3 to 1.8 sulfonic acid groups per aromatic nucleus. Particularly, suitable polymers which contain sulfonic acid groups are copolymers of aromatic monovinyl compounds with aromatic polyvinyl compounds, particularly, divinyl compounds, in which the polyvinyl benzene content is preferably 1 to 20% by weight of the copolymer (see, for example, German Patent specification 908,247).

The ion exchange resin is preferably used in a granular size of about 0.25 to 1 mm, although particles form 0.15 mm up to about 1 mm may be employed.

The resin catalyst is loaded into the straight pass fixed bed reactor as a fixed bed of the granules. The feed to the reaction is fed to the bed in liquid phase. The bed may be horizontal, vertical or angled. Preferably the bed is vertical with the feed passing downward through the bed and exiting, after reaction, through the lower end of the reactor.

A preferred catalytic distillation structure for use herein comprises placing the cation exchange resin particles into a plurality of pockets in a cloth belt, which is supported in the distillation column reactor by open mesh knitted stainless steel wire by twisting the two together in a helical form. This allows the requisite flows and prevents loss of catalyst. The cloth may be any material which is inert in the reaction. Cotton or linen are useful, but fiber glass cloth or "Teflon" cloth are preferred.

ISOMERIZATION

Isomerization of mono-olefins may be broken down into two separate and distinct reactions. In the first type the location of the double bond in a linear or normal olefin is shifted with the olefin remaining linear. This type isomerization is that described above during the diene hydrogenation. In the second type of the carbons with its attendant hydrogen is shifted to make an iso-olefin from a linear olefin. The latter is termed skeletal isomerization and the process employed in the present invention in this step.

Zeolitic catalyst such as ZSM-22, ZSM-23, ZSM-35, ZSM-5, ZSM-11, ZSM-38 and ZSM-48 have been used as isomerization catalyst. ZSM-35, an isotype of ferrierite has been identified as one of the better zeolites for this purpose. A number of these catalyst are discussed in U.S. Pat. Nos. 3,992,466; 4,922,048; 4,996,925; 4,996,386 and 5,449,851

Generally alumina isomerization catalysts have a surface area of at least about 100 $m^2/g$, preferably the surface area is greater than 150 $m^2/g$. Techniques of preparing such alumina catalysts are well known in the art. Examples of such alumina catalysts include eta-alumina and gamma-alumina.

The best alumina isomerization catalysts are those aluminas having high purity, particularly with respect to their content of alkali metals. Thus generally the aluminas should contain less than about 0.1 weight percent alkali metal, preferably less than 0.05 weight percent, based on the weight of the catalyst. The alkali metals include lithium, sodium, potassium, rubidium, and cesium.

The isomerization catalysts, e.g. zeolites or alumina, can be employed in the manner known in the art for the skeletal isomerization of olefins to more highly branched olefins. Such catalysts are particularly suitable for the isomerization of n-olefins having 4 to 10 carbon atoms per molecule or mixtures thereof. Mixtures comprising olefins and essentially inert hydrocarbons can also be treated according to this invention to provide an isomerized olefinic product in admixture with the inert hydrocarbons. Particularly useful isomerizations with such catalysts are conducted on feedstreams of gasoline, especially catalytically cracked gasoline.

This isomerization with such catalysts can be conducted under any conditions sufficient to produce the desired isomers. Generally the isomerization is conducted at a temperature in the range of about 315° C. to about 510° C., preferably about 343° C. to about 454° C. for alumina and 200°–600° C. for the zeolites, e.g. ZSM-35 the preferred temperature is 390°–550° C. Isomerization is generally not affected significantly by pressure, but elevated pressures can accelerate some undesirable olefin reactions, such as polymerization. Hence low reaction pressure is generally favored. Partial pressure of the hydrocarbon during the isomerization generally will be in the range of about atmospheric to about 200 psig (i.e. about $1.03 \times 10^5$ Pa to about $148 \times 10^6$ Pa) more preferably the reaction pressure for isomerization does not exceed 100 psig ($7.9 \times 10^5$ Pa). Typically the contact time for the hydrocarbon in such isomerization reactions, expressed in volumes of liquid feedstock per volume of catalyst per hour (LHSV), is in the range of about 0.1 to about 15, preferably about 0.5 to about 5.

Methanol is believed to have a deactivating effect on the alumina catalyst by creating carbon deposits on the catalyst surface which deactivate the most active sites. Therefore, overall catalyst activity and conversion are reduced, but selectivity toward isomerization is increased.

The feeds are any of those alkenes which are vapors under the conditions specified above. $C_4$'s, $C_5$'s and $C_6$'s are particularly suit for this process.

Gamma alumina is preferred, preferably of high purity, particularly less than 0.01% NaO.

When the activity of the catalyst has declined below a desired level the flow of hydrocarbon to the catalyst is stopped and the catalyst is regenerated.

Generally the regeneration involves contacting the deactivated catalyst with steam and free oxygen-containing gas at a temperature in the range of about 425° C. to about 705° C., preferably at a temperature no greater than 650° C. Pressure is not critical to the process of oxidative regeneration but elevated pressure, e.g. pressures in the range of about 50 to about 200 psig (about $4.5 \times 10^5$ to about $1.48 \times 10^6$ Pa) may be desirable for economic reasons.

The free oxygen-containing gas can include air or, preferably, air which has been further diluted with an inert gas such as nitrogen. Water can be added to the free oxygen-containing gas in any suitable manner. For example steam can be added to the free oxygen-containing gas.

The advantage of the present isomerization process is illustrated by a run containing 0.03 wt. % methanol with a $C_5$ feed containing about 26 wt. % normal $C_5^=$'s and 5 wt. % iso $C_5^=$'s after about 4 hours on stream gave consistently 70 to 80% selectivity to isoamylene, compared to a feed without methanol which gave an average of 50 to 60%

The following table shows the results of isomerization of alkene containing $C_5$ stream by contacting the $C_5$ stream with an alumina catalyst. The contact was carried out in a fixed catalyst bed reactor at temperatures between 663°–692° K. After 132 hours on stream, 4 ml (cc) of methanol (MeOH) was injected into the $C_5$ feed stream prior to contact with the alumina catalyst. An amount of methanol equal to 0.17% of the volume of the catalyst is injected into the flowing feed to the reactor over a one minute period. Two (2) hours after the methanol was injected, the $C_5^=$ conversion was reduced from 72.6% but selectivity to iso-$C_5^=$'s was increased to 74.1%, from 63.8.

The reactor temperature was increased to 693° K. at time 165 hours on stream, which resulted in an increase in conversion to 70.0%, and a yield increase from 44% to 49%. The higher temperature lowered selectivity from 70 percent to 68 percent, which is still 5% higher than the untreated catalyst. Conditions for the runs are reported in TABLE II and the results are reported in TABLE III.

TABLE II

| RUN | 1 | 2 | 3 | 4 | 5 | 6 |
| --- | --- | --- | --- | --- | --- | --- |
| Hrs. on Stream | 132 | 135.5 | 140 | 165 | 171 | 177 |
| CAT. WT. G. | 141.700 | 141.700 | 141.700 | 141.700 | 141.700 | 141.700 |
| Feed Source | TAME OH | TAME OH | TAME OH | TAME OH | TAME OH | TAME OH |
| RX. LTH. (FT) | 18.000 | 18.000 | 18.000 | 18.000 | 18.000 | 18.000 |
| RX. ID. (IN) | 0.305 | 0.305 | 0.305 | 0.305 | 0.305 | 0.305 |
| RX. VOL. (cc) | 258.610 | 258.610 | 258.610 | 258.610 | 258.610 | 258.610 |
| CAT. VOL. (cc) | 236 | 236 | 236 | 236 | 236 | 236 |
| Bath Temp, F. | 738.0 | 739.0 | 738.0 | 788.0 | 788.0 | 790.0 |
| Rx. Temp. K. | 665.422 | 665.978 | 665.422 | 693.200 | 693.200 | 694.311 |
| Contact Time, sec. | 9.299 | 9.129 | 9.217 | 8.386 | 8.604 | 7.954 |
| Pressure, psig | 38.00 | 38.00 | 38.00 | 37.00 | 37.00 | 34.00 |
| Feed, ml/min | 11.3 | 11.5 | 11.4 | 11.8 | 11.5 | 11.7 |
| F/W, g./g. cat/*hr. | 2.967 | 3.019 | 2.993 | 3.098 | 3.019 | 3.072 |
| Feed, L/hr. STP | 134.599 | 136.982 | 135.790 | 140.555 | 136.982 | 139.364 |
| Feed, L/hr. @Rxt conditions | 91.446 | 93.142 | 92.256 | 101.403 | 98.825 | 106.908 |
| Linear vel. ft/sec | 1.767 | 1.799 | 1.782 | 1.959 | 1.909 | 2.065 |

TABLE III

| RUN | FEED | 1 | 2 | 3 | 4 | 5 | 6 |
| --- | --- | --- | --- | --- | --- | --- | --- |
| Hrs. on Stream | | 132 | 135.5 | 140 | 165 | 171 | 177 |
| C2- | 0.000 | 0.030 | 0.030 | 0.020 | 0.020 | 0.020 | 0.020 |
| C2 | 0.000 | 0.000 | 0.000 | 0.000 | 0.000 | 0.000 | 0.000 |
| C3- | 0.020 | 0.440 | 0.350 | 0.260 | 0.390 | 0.390 | 0.440 |
| C3 | 0.040 | 0.040 | 0.040 | 0.030 | 0.030 | 0.030 | 0.040 |
| DME | 0.180 | 0.000 | 0.000 | 0.000 | 0.000 | 0.000 | 0.000 |
| IB | 0.010 | 3.130 | 1.650 | 1.570 | 2.880 | 2.910 | 3.000 |

TABLE III-continued

| RUN | FEED | 1 | 2 | 3 | 4 | 5 | 6 |
|---|---|---|---|---|---|---|---|
| B-1 | 0.430 | 1.420 | 1.610 | 1.490 | 1.410 | 1.390 | 1.400 |
| BD | 0.010 | 0.000 | 0.000 | 0.000 | 0.010 | 0.000 | 0.000 |
| trB2 | 1.990 | 2.590 | 3.050 | 2.900 | 2.450 | 2.390 | 2.410 |
| cB2 | 4.290 | 1.770 | 2.090 | 1.990 | 1.710 | 1.610 | 1.680 |
| nC4 | 3.270 | 1.950 | 1.890 | 1.800 | 1.900 | 1.880 | 1.910 |
| 3MB1 | 1.310 | 0.760 | 0.730 | 0.720 | 0.820 | 0.810 | 0.820 |
| i-C5 | 48.290 | 48.430 | 48.300 | 48.220 | 49.230 | 49.420 | 49.280 |
| Pe1 | 2.900 | 1.120 | 1.650 | 1.690 | 1.270 | 1.230 | 1.230 |
| 2MB1 | 0.340 | 5.070 | 4.880 | 4.890 | 5.190 | 5.190 | 5.170 |
| nC5 | 8.850 | 8.890 | 8.920 | 9.010 | 9.150 | 9.180 | 9.140 |
| 2MB1,3 | 0.000 | 0.000 | 0.000 | 0.000 | 0.000 | 0.000 | 0.000 |
| tPe2 | 17.600 | 4.030 | 5.980 | 6.180 | 4.300 | 4.140 | 4.100 |
| UNK1 | 0.040 | 0.010 | 0.010 | 0.010 | 0.010 | 0.010 | 0.030 |
| cPe2 | 6.190 | 2.020 | 3.000 | 3.100 | 2.200 | 2.120 | 2.110 |
| 2MB2 | 3.220 | 12.470 | 12.080 | 12.220 | 12.110 | 12.060 | 12.010 |
| tPIP | 0.000 | 0.000 | 0.000 | 0.000 | 0.000 | 0.000 | 0.000 |
| cPIP | 0.000 | 0.000 | 0.000 | 0.000 | 0.000 | 0.000 | 0.000 |
| CyCs | 0.020 | 0.020 | 0.020 | 0.020 | 0.030 | 0.020 | 0.030 |
| UNK2 | 0.540 | 0.910 | 0.780 | 0.780 | 0.890 | 0.910 | 0.890 |
| HVY | 0.000 | 4.350 | 2.480 | 2.680 | 3.540 | 3.740 | 3.850 |
| TOTAL | 100.000 | 100.000 | 100.000 | 100.000 | 100.000 | 100.000 | 100.000 |
| Total $nC_5^=$, wt % | 26.690 | 7.170 | 10.630 | 10.970 | 7.770 | 7.490 | 7.440 |
| Total $iC_5^=$, wt % | 4,870 | 18.300 | 17.690 | 17.830 | 18.120 | 18.060 | 18.000 |
| % $nC_5^=$'s CONVERSION | | 72.592 | 59.365 | 58.066 | 70.888 | 71.937 | 72.124 |
| Selectivity to $iC_5^=$'s | | 63.823 | 74.115 | 76.695 | 70.032 | 68.698 | 68.208 |
| SUM 2MB1 + 2MB2 | | 17.540 | 16.960 | 17.110 | 17.300 | 17.250 | 17.180 |
| C6&C7 + HVY's | | 5.260 | 3.260 | 3.460 | 4.430 | 4.650 | 4.740 |
| Contact Time | | 9.299 | 9.129 | 9.217 | 8.386 | 8.604 | 7.954 |
| YIELD (Conv. × Select) | | 46.33 | 44.00 | 44.53 | 49.64 | 49.42 | 49.19 |

Figure 1:
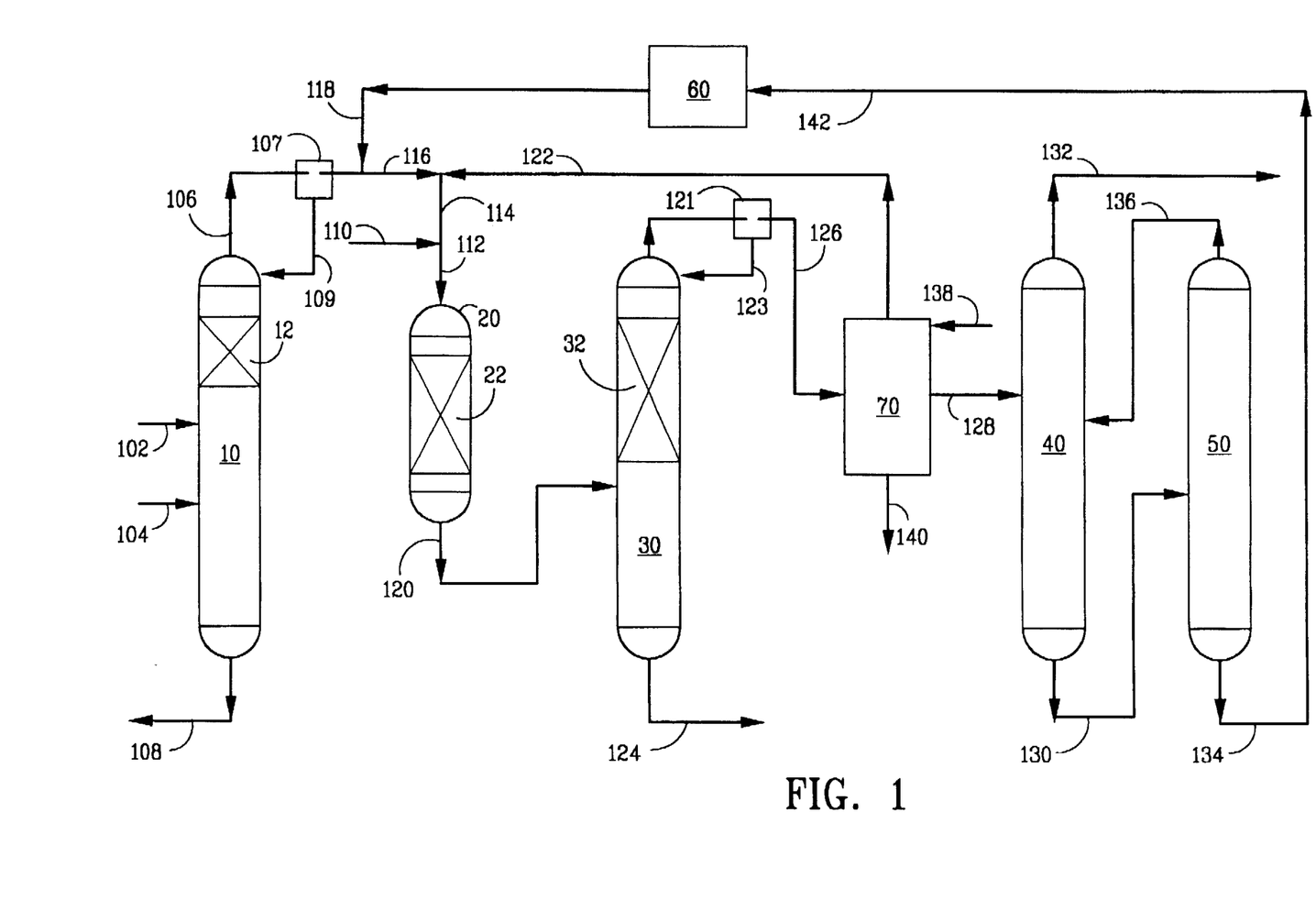
FIG. 1 is simplified schematic of an embodiment having an iso/normal olefin separation and one etherification unit.

Referring to FIG. 1 hydrogen and FCC light naphtha are fed to a first distillation column reactor 10 through flow lines 104 and 102 respectively. In the lower section of the distillation column reactor the $C_6+$ material is separated from the $C_5$ and lighter hydrocarbons contained in the light naphtha. The $C_6+$ material is withdrawn from the column 10 as bottoms via flow line 108 and sent to gasoline blending. The $C_5$ and lighter materials are distilled upward into a distillation reaction zone 12 containing a hydrogenation catalyst in the form of a catalytic distillation structure.

In the distillation reaction zone 12 the diolefins are hydrogenated to mono-olefins. The conditions in the column 10 are adjusted such that little if any hydrogenation of the mono-olefins occurs. Typically the column 10 will be operated at a pressure of 0 to 250 psig and at a temperature within the distillation reaction zone of between 100° and 300° F. Sufficient hydrogen is supplied to support the reaction but kept below that which would cause jet flooding of the column which is understood to be the "effectuating amount of hydrogen" as the term is used herein. Generally the mole ratio of hydrogen to diolefins in the feed to the fixed bed of the present invention will be at least 1 to 1, preferably 2 to 1. In addition to hydrogenating the diolefins, the catalyst also isomerizes some of the 3-methyl butene-1 to either 2-methyl butene-1 or 2-methyl butene-2. This is important because 3-methyl butene-1 does not react with methanol to form TAME while the other two isomers do.

The hydrogenated product containing essentially no diolefins and lesser amounts of 3-methyl butene-1 is withdrawn as overheads via flow line 106. A condenser 107 and reflux system 109 returns a portion of the overhead as reflux. The overheads in line 106 contain predominantly $C_5$'s which includes iso and normal $C_5^=$'s and iso and normal $C_5$'s. A recycle $C_5$ stream 118 is combined with the overheads to make stream 116 to which is added recycle methanol via line 122 for combined stream in line 114. Make up methanol is added via line 110 to flow line 114 to make the composition in flow line 112 equal the sum of the hydrogenated stream from the first distillation column reactor, the recycle $C_5$ stream, the recycle methanol stream and the make up methanol stream.

The combined feed in flow line 112 is fed to a boiling point reactor 20 containing a fixed bed of an acidic cation exchange resin 22, such as Amberlyst 15, where a substantial portion of the $iC_5^=$'s are reacted with an excess of methanol to form TAME. The boiling point reactor 20 is operated at a pressure such that the mixture is boiling within the catalyst bed 22. The exothermic heat of reaction is absorbed as latent heat of vaporization preventing a temperature increase across the reactor.

The effluent from the fixed bed reactor 20 is fed via flow line 120 to a second distillation column reactor 30 having a second distillation reaction zone 32 containing a second catalytic distillation structure comprising the same catalyst as in the fixed bed reactor in the same arrangement as the catalyst in the first column 10. The remainder of the unreacted $iC_5^=$'s are reacted with unreacted methanol to produce more TAME which is distilled downward out of the distillation reaction zone 32 and eventually removed as bottoms via flow line 124.

The overheads from the second distillation column reactor 30 containing methanol and inerts (unreacted $nC_5^=$'s and $C_5$ alkanes) are taken overhead via flow line 126 and sent to a water wash system 70 where the methanol is removed and recycled to the fixed bed reactor 20 via flow line 122. Lines 138 and 140 are, respectively, water supply and wash water recovery. The $C_5$ hydrocarbons are then passed via flow line 128 to a separation system where the $nC_5^=$'s are separated from the $C_5$ alkanes. The system shown is an extractive distillation system wherein a solvent is used in a first column 40 to effect the separation. Conventional solvents for this purpose include acetonitrile, dimethyformamide, N-methylpyrrolidone, β-methoxypropionitrile, dimethylacetamide, dimethyl sulfoxide and τ-butyrolactone. The solvent is separated from the $nC_5^=$'s in a second distillation column 50 via flow line 130 and recycled to the first via flow line 136. The $C_5$ alkanes are removed from the first column 40 as overheads via flow line 132 and recovered. The $nC_5^=$'s are recovered as bottoms from the second distillation column 50 via flow line 134 and passed to a skeletal isomerization unit 60 wherein a portion of the $nC_5^=$'s are skeletally isomerized to $iC_5^=$'s, the whole being recycled to the fixed bed reactor via flow line 118. Since the water wash is used and operated to remove substantially all of the methanol, methanol in accordance with the present invention may be added to the feed to the isomerization unit 60 by line 142 to mix in the feed or through a separate line not shown. Because the isomerization unit 60 does not accomplish 100% conversion of the $nC_5^=$'s a slip stream (not shown) to remove a portion of the $C_5^=$'s from flow line 134 is required to prevent build up of the $nC_5^=$'s in the system.

Typical operational parameters for the hydrogenation reactor 10 using a palladium catalyst are pressure 200 psig, temperature 260° F., $H_2$:olefin ratio=2:1 and for the isomerization reactor 60 using an alumina catalyst pressure 50–60 psig, temperature 730°–820° F. LHSV 1.5–4.0.

TABLE IV below follows the flow in FIG. 1 of the light naphtha stream, particularly the $C_5$ containing portion through the hydrogenation reactor, the TAME reactors, the alkane/olefin separation and the skeletal isomerization unit. The conditions in the TAME reactor(s) can be adjusted to obtain essentially 100% conversion of the 2-methyl butene-1 and 2-methyl butene-2. The combined processes result in a conversion of the two isomers to TAME in the range of 130% based on the two isomers in the initial feed. Additionally the olefin content of the final product which might be sent to gasoline blending is reduced substantially—by about 85%.

It should be appreciated that the equipment necessary to achieve the desired conditions, flow rates and separations are well within the expertise of a practicing engineer and such details are omitted for simplicity.

TABLE IV

| STREAM | 102 | 106 | 128 | 134 | 118 |
|---|---|---|---|---|---|
| Component, wt % | | | | | |
| Lights | 0.073 | 0.000 | 0.000 | 0.000 | 0.000 |
| Dimethyl ether | 0.003 | 0.002 | 0.000 | 0.000 | 0.000 |
| isobutane | 0.488 | 0.093 | 0.093 | 0.000 | 0.000 |
| methanol | 0.058 | 0.000 | 0.000 | 0.000 | 0.000 |
| Other $C_4$'s | 4.573 | 3.304 | 3.304 | 0.000 | 0.000 |
| 3-methyl butene-1 | 1.026 | 0.270 | 0.270 | 0.270 | 0.376 |
| isopentane | 31.974 | 32.066 | 32.066 | 0.000 | 0.000 |
| pentene-1 | 2.708 | 0.962 | 0.962 | 0.962 | 1.273 |
| 2-methyl butene-1 | 6.496 | 4.012 | 0.000 | 0.000 | 1.976 |
| normal pentane | 3.848 | 4.061 | 4.061 | 0.000 | 0.000 |
| 2-methyl butadiene-1,3 | 0.147 | 0.002 | 0.002 | 0.000 | 0.000 |
| trans pentene-2 | 6.995 | 9.066 | 9.066 | 9.066 | 2.446 |
| Unknown 1 | 0.138 | 0.094 | 0.094 | 0.000 | 0.000 |
| cis pentene-2 | 3.886 | 3.723 | 3.723 | 3.723 | 2.200 |
| 2-methyl butene-2 | 11.634 | 14.083 | 0.000 | 0.000 | 3.431 |
| trans piperylene | 0.142 | 0.002 | 0.002 | 0.000 | 0.000 |

TABLE IV-continued

| STREAM | 102 | 106 | 128 | 134 | 118 |
|---|---|---|---|---|---|
| cis piperylene | 0.095 | 0.003 | 0.003 | 0.000 | 0.000 |
| cyclo-$C_5$ | 0.001 | 0.058 | 0.058 | 0.000 | 0.000 |
| $C_6^+$ | 25.603 | 0.000 | 0.000 | 0.000 | 0.000 |
| Total | 100.000 | 74.397 | 53.701 | 14.021 | 11.702 |

Figure 2:
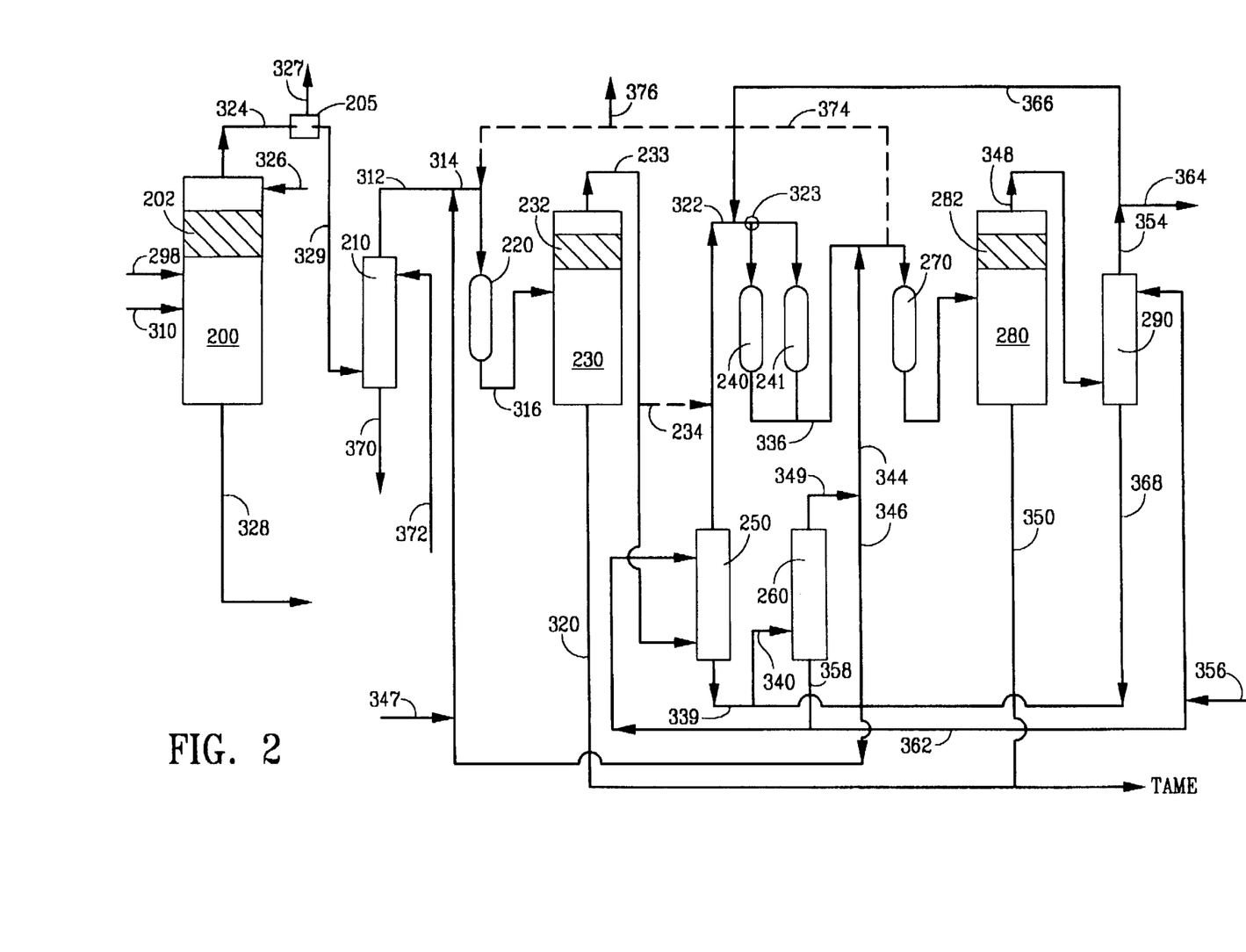
FIG. 2 is a simplified flow diagram of an embodiment of the present invention employing two etherification units and eliminating the extraction.

FIG. 2 shows an embodiment alternatively employing a second etherification reactor systems (270/280) and eliminating the solvent extraction.

The light naphtha is fed via line 310 to the distillation column reactor 200 below the catalyst packing 202. Distillation column reactor 200 containing a packing of suitable hydrogenation catalyst as part of a distillation structure 202, as in the wire mesh arrangement described above. The column may also have standard distillation structure (not shown).

The hydrogen is fed as a gas via flow line 298 at or near the bottom of the bed of catalyst packing 202 as described above. Heat may be added to the bottoms by circulating through reboiler (not shown). After the reaction has started the heat of reaction, which is exothermic, causes additional vaporization of the mixture in the bed. Vapors are taken overhead through flow line 324 and passed to condenser/reflux drum 205 where substantially all of the condensible material is condensed to a temperature of 100° F. and collected and separated from non condensibles, such as the unreacted hydrogen. The uncondensible material is vented from the reflux drum via flow line 327.

A portion of the condensed materials collected in the reflux drum are returned to the top of the distillation column reactor 200 via flow line 326. The remaining portion of the condensed overhead passes via line 329 to water was column where the liquid feed is washed in countercurrent flow with water from 372. The waste water exits via line 370 for further treatment.

The feed passes from the water wash via line 312 and mixes with methanol or other suitable alcohol from line 346, which is either recycled from down stream or added as make-up via line 347, and into guard bed reactor 220 operated substantially isothermally at 0–400 psig and 120°–300° F. at high LHSV (i.e. 5–20). The alcohol is preferably methanol, although ethanol and propanol may be used to similar effect. Generally the alcohol is present in a stoichiometric amount up to 10% excess, based on the isoolefin. The pressure in reactor 220 is controlled by the pressure in catalytic distillation reactor 230. The reactor 220 is operated at a temperature such that a portion but less than all of the reaction mixture is in the vapor phase. This mixture which contains from about 80–90% ether produced from the isoamylene in the feed passes via line 316 directly into the catalytic distillation reactor 230 at a point below the bed of catalyst prepared as distillation structures as described above in FIG. 1, where the etherification proceeds to 97+% conversion of the isoamylene.

In addition to the catalytic distillation structures the column may contain convention distillation structures, e.g. trays (not shown). The product tertiary amyl methyl ether (TAME) is separated by the concurrent fractionation in the reactor 230 and is recovered as bottoms stream 320. The lighter material, primarily unreacted component of the $C_5$ feed form the overheads 233. This steam contains $C_5$ olefins and alkane as well as azeotroped alcohol and some by-products. This mixtures passes to water wash column 250 where water from line 362 contacts the overhead in countercurrent flow to remove methanol and other water soluble impurities. The wash water goes to methanol recovery column 260 where it is separated by distillation. The methanol is striped out and passes overhead 349 with a portion recycling via 346 to the first guard bed reactor 220 and a portion 344 going to a second guard bed reactor 270 and CD reactor 280 system. The water is recovered and recycled vial 362 or sent to a third wash water column 290 via 362. Make-up water is added through line 346.

In some operations the water wash may be omitted and the overhead 233 passed via 234 directly to the isomerization units 240 or 241 where the entrained methanol is used to modify the isomerization catalyst. If an intermittent methanol treatment is being used, then the methanol in the overheads 233 is removed and the appropriate amounts of methanol added either to the feed 322 or directly to the isomerization reactor.

The overhead 322 from the water wash (or the etherification unit) is directed by valve 323 to either isomerization reactor 240 or 241. This recognizes the short run period before the isomerization catalyst cokes up compared to the catalyst run life in the other components of the present integrated system and allows one isomerization unit to regenerate while the other runs.

High purity gamma alumina is used as extrudate of about 1/16" at a temperature in the range of 730°–830° F. at 30–50 psig and WHSV of 1.5 to 2.5 which can remain on stream about 100 and be regenerated with steam for about 24 hours at 780°–850° F. A portion of the normal pentenes in the feed to the isomerization reactor are converted to isoamylene, which is fed directly to the second guard bed reactor 270 by 336 and hence by 346 with methanol added via 344 to the catalytic distillation reactor 280 just below the catalytic distillation structures 282. The operation of the second etherification section is generally the same as the first. The methanol and isoamylene selectively react to form TAME which is recovered as bottoms 350 with the overheads 348 going to the third water wash column 290 for recovery of methanol. A portion of the recovered $C_5$'s from the water wash are recycled via 366 to the isomerization reactors and a portion withdrawn via line 364 for gasoline blending.

Bottoms product containing essentially no $C_5$ diolefins is withdrawn via flow line 328 and may be sent to gasoline blending as stable gasoline.

The invention claimed is:

1. An integrated process for producing TAME comprising the steps of:
   (a) feeding a first stream comprising a naphtha and a second stream comprising hydrogen to a first distillation column reactor containing a hydrogenation catalyst in a first catalytic distillation structure in the upper portion thereof and inert distillation structure in the lower portion thereof;
   (b) concurrently in said first distillation column reactor
      (i) separating the fraction of said naphtha containing $C_5$'s and lower boiling materials from $C_6$ and higher boiling materials in said lower portion by fractional distillation, said $C_5$ containing fraction comprising $iC_5$'s, $nC_5$'s, $iC_5^=$'s, $nC_5^=$'s, and $C_5$ diolefinic materials,
      (ii) contacting said $C_5$ containing fraction with said catalytic distillation structure to react said $C_5$ diolefinic materials contained within $C_5$ containing fraction with said hydrogen to convert said diolefinic materials to mono-olefins,
      (iii) removing said $C_6$ and higher boiling materials from said first distillation column reactor as a first bottoms, and
      (iv) removing said $C_5$ containing fraction from said distillation column reactor as a first overheads;
   (c) feeding said first overheads and a stream containing methanol to a first straight pass fixed bed etherification reactor containing an acid cation exchange resin to react a portion of the $iC_5^=$'s with said methanol to produce an effluent containing tertiary amyl methyl ether, methanol and unreacted $iC_5^=$'s and other unreacted materials;
   (d) feeding said effluent to a second distillation column reactor containing a second catalytic distillation structure comprising an acid cation exchange resin;
   (e) concurrently in said second distillation column reactor:
      (i) contacting said effluent with said second catalytic distillation structure thereby reacting a portion of said $iC_5^=$'s with methanol to form additional tertiary amyl methyl ether,
      (ii) separating methanol and the remaining unreacted materials from the tertiary amyl methyl ether produced in said first fixed bed reactor and in said second distillation column reactor by fractional distillation,
      (iii) recovering said tertiary amyl methyl ether as a second bottoms from said second distillation column reactor, and
      (iv) recovering said methanol and remaining unreacted materials comprising $nC_5^=$ as a second overheads; and
   (f) feeding said second overheads to a straight pass fixed bed reactor containing an isomerization catalyst to produce $iC_5^=$'s.

2. The process according to claim 1 wherein said isomerization catalyst is an alumina treated with methanol.

3. The process according to claim 1 further comprising:
   (g) feeding said effluent from (f) and methanol to a second straight pass fixed bed reactor etherification reactor containing an acid cation exchange resin to react a portion of the $iC_5^=$'s with said methanol to produce an effluent containing tertiary amyl methyl ether, methanol and unreacted $iC_5^=$'s and other unreacted materials;
   (h) feeding said effluent from said second straight pass etherification reactor to a distillation column reactor containing a third catalytic distillation structure comprising an acid cation exchange resin; and
   (i) concurrently in said third distillation column reactor:
      (i) contacting said effluent from (g) with said third catalytic distillation structure thereby reacting a portion of said $iC_5^=$'s with methanol to form additional tertiary amyl methyl ether,
      (ii) separating methanol and the remaining unreacted materials from the tertiary amyl methyl ether produced in said second fixed bed reactor and in said third distillation column reactor by fractional distillation,
      (iii) recovering said tertiary amyl methyl ether as a second bottoms from said third distillation column reactor, and
      (iv) recovering said methanol and remaining unreacted materials as a second overheads.

4. The process according to claim 1 wherein said first catalytic distillation structure comprises a supported palladium catalyst on an alumina base contained within a plurality of flexible wire mesh containers.

5. The process according to claim 1 wherein the $iC_5^=$'s contained within said first stream comprise 3 methyl butene-1, 2 methyl butene-1, and 2 methyl butene-2, and a portion of said 3 methyl butene-1 is converted to 2 methyl butene-1 or 2 methyl butene-2 in said first distillation column reactor and substantially all of said 2 methyl butene-1 and 2 methyl butene-2 react with said methanol in said fixed reactor and said second distillation column reactor to form tertiary amyl alcohol.

6. The process according to claim 1 wherein the second overhead from (d) is fed to water wash to remove methanol then to an extractive distillation to separate and recover $iC_5^=$ from $C_5$ alkanes and the recovered $iC_5^=$ are used as the feed in (f).

7. The process according to claim 6 wherein the product from the isomerization reactor is recycled to the first straight pass fixed bed etherification reactor containing an acid cation exchange resin.

8. In an integrated process for the production of ethers comprising hydrogenating a $C_5$ naphtha cut containing $iC_5^=$, $nC_5^=$, $C_5$ alkanes and diolefins to remove the diolefins; recovering the hydrogenated $C_5$ naphtha cut and contacting the cut and a $C_1$–$C_4$ alcohol with an etherification catalyst to selectively react said $iC_5^=$ with said alcohol to produce an ether; separating the ether from said cut and contacting said cut with an isomerization catalyst to isomerize $nC_5^=$ to $iC_5=$; wherein the improvement comprises using as the isomerization catalyst alumina treated with methanol.

9. The process according to claim 8 wherein said methanol treatment is continuous with said contacting.

10. The process according to claim 8 wherein said methanol treatment is intermittent.

11. The process according to claim 5 wherein said methanol treatment is prior to said contacting.

12. A process for the isomerization of normal alkenes to isoalkenes comprising the steps of:

(a) adding to a feed stream comprising alkenes over an alumina catalyst treated with methanol to improve selectivity to said isoalkenes under skeletal isomerization conditions to effect isomerization of said alkenes to said isoalkenes.

13. The process according to claim 12 wherein said normal alkenes comprise normal pentenes and a isomerization product comprising isoamylenes is produced.

14. The process according to claim 12 wherein methanol is added to said feed stream of alkenes in an amount of from about 0.001 to 0.1 weight percent of the feed stream.

15. The process according to claim 12 wherein said alumina catalyst is gamma alumina.

\* \* \* \* \*